(12) United States Patent
Pessin

(10) Patent No.: US 8,109,938 B2
(45) Date of Patent: Feb. 7, 2012

(54) OPHTHALMIC IMPLANT INJECTOR AND FOLDING CARTRIDGE

(75) Inventor: Olivier Pessin, Grezieu la Varenne (FR)

(73) Assignee: Sedat, Irigny (FR)

( * ) Notice: Subject to any disclaimer, the term of this patent is extended or adjusted under 35 U.S.C. 154(b) by 321 days.

(21) Appl. No.: 12/093,017

(22) PCT Filed: Nov. 9, 2006

(86) PCT No.: PCT/FR2006/002499
§ 371 (c)(1),
(2), (4) Date: Jun. 17, 2008

(87) PCT Pub. No.: WO2007/054645
PCT Pub. Date: May 18, 2007

(65) Prior Publication Data
US 2008/0281333 A1 Nov. 13, 2008

(30) Foreign Application Priority Data
Nov. 9, 2005 (FR) .................................. 05 11421

(51) Int. Cl.
*A61F 9/00* (2006.01)
(52) U.S. Cl. .................... 606/107; 623/6.12; 623/6.11
(58) Field of Classification Search ............... 623/6.12, 623/4.1, 5.11, 5.14–5.16, 6.41, 6.43, 6.44, 623/6.38, 907; 606/107, 106, 204.25
See application file for complete search history.

(56) References Cited

U.S. PATENT DOCUMENTS

| | | | | |
|---|---|---|---|---|
| 6,129,733 A | * | 10/2000 | Brady et al. ................ | 606/107 |
| 6,142,999 A | | 11/2000 | Brady et al. | |
| 2005/0065534 A1 | * | 3/2005 | Hohl ............................ | 606/107 |
| 2008/0119864 A1 | * | 5/2008 | Deinzer et al. ............... | 606/107 |

FOREIGN PATENT DOCUMENTS

| | | | |
|---|---|---|---|
| EP | 1502559 A1 | * | 2/2005 |
| WO | 02074208 A2 | | 9/2002 |
| WO | 03044946 A2 | | 5/2003 |
| WO | 2005082284 A1 | | 9/2005 |
| WO | 2005082285 A1 | | 9/2005 |
| WO | WO2005082285 | * | 9/2005 |

\* cited by examiner

*Primary Examiner* — Ryan Severson
*Assistant Examiner* — Tin Nguyen
(74) *Attorney, Agent, or Firm* — Sughrue Mion, PLLC

(57) ABSTRACT

A cartridge for folding an ophthalmic implant including pliers having two articulated arms which are provided with substantially coaxial channels and each of which is boarded by two longitudinal edges. The channels are open in front of each other and define a partially folded conduit containing the implant when the two arms are brought to each other. When the two arms are brought to each other, at least two edges positioned in front of the channels are driven apart transversally with respect to a conduit on a plane. The two arms are jointed in such a way that the arm delimits the supporting shoulder of the implant being projected in front of the channel embodied in the other arm.

10 Claims, 4 Drawing Sheets

OPHTHALMIC IMPLANT INJECTOR AND FOLDING CARTRIDGE

The present invention relates to a cartridge for folding an ophthalmic implant.

It is known in the treatment of cataracts for a surgeon to insert into the eye of a patient an ophthalmic implant in the shape of, for example, a lens provided laterally with two diametrically opposed curved arms.

The implant is inserted into the eye of a patient by means of an injection cannula which is pushed by a piston through said cannula. In order to pass through the cannula, the implant is spirally curled on itself about a diametrical direction connecting the two arms of the implant.

The spiral curling of the implant is referred to as folding and is carried out in a folding cartridge. Said cartridge comprises the injection cannula and can be inserted, after being loaded, onto an injection mechanism comprising a support element and a sliding plunger.

Known folding cartridges comprise two arms which are articulated relative to one another so as to form a clamp. Next to the articulation, each arm has a semi-cylindrical channel extending parallel to the axis of articulation. The channels of the two arms open opposite one another in such a way that when the two arms are closed together the channels form a conduit containing the implant. The semi-circular cross-section of the channels means that when the two arms are closed together the lens constituting the implant is folded in on itself in such a way that the end edges are closed together so as to face one another.

The implant is curled on itself so as to form a spiral by pushing the implant through the cannula which, for this purpose, has a conical internal surface, of which the diameter varies from the conduit containing the implant to the exit end.

The implant thus begins to spirally curl when the two arms are closed together whilst the implant is held between the two channels.

The two channels ensure that the opposite edges of the implant are closed together in such a way that the implant substantially forms a cylinder. To form a spiral the two opposite edges must overlap, one passing inside and the other passing outside. This overlapping is random in either direction, in particular depending on the initial positioning of the implant by the surgeon between the two channels.

In addition, in some circumstances, the two edges are exactly opposite one another while the two arms are closed together in such a way that when the implant enters into the cannula with a conical inner profile, the two edges are pressed against one another which could damage the implant.

The object of the invention is to provide a folding cartridge which does not damage the implant during the phase of folding thereof.

For this reason, the invention relates to a folding cartridge of the aforementioned type, characterised in that when the two arms have been closed together at least two of the edges facing the two channels are displaced transversely relative to the conduit in the joining plane of the two arms in such a way that one arm defines a shoulder which supports the implant and projects opposite the channel arranged in the other arm.

According to particular embodiments, the cartridge comprises one or more of the following characteristics:

- in the joining plane, the shoulder is on average between 0.1 and 0.8 mm wide, measured transversely to the direction of the channels;
- the two displaced edges are further away from the axis of articulation of the two arms than the two other edges which meet when the two arms are closed together;
- the cartridge comprises an injection cannula, of which the internal surface converges into the extension of the conduit containing the implant when the two arms are closed together;
- the two channels have a substantially semi-circular or semi-elliptical cross-section;
- the shoulder is substantially planar and the axis of the conduit formed by the two channels extends substantially into the plane defined by the shoulder;
- each arm has, beyond the channel and on the side opposite to the axis of articulation, a manoeuvring flange and the shoulder extends a flange for manoeuvring one of the arms; and
- the two arms comprise, next to the edges of the channels and outside the channels, complementary projecting and hollow connection profiles which are of such a size that the profiles fit together when the two arms are closed together.

The invention also relates to an implant injector comprising a cartridge as disclosed above and an injection mechanism comprising a body for linking to the cartridge and a plunger capable of pushing the implant contained inside the cartridge.

The invention will be better understood by reading the following description, given solely by way of example and with reference to the drawings, in which.

Figure 1:
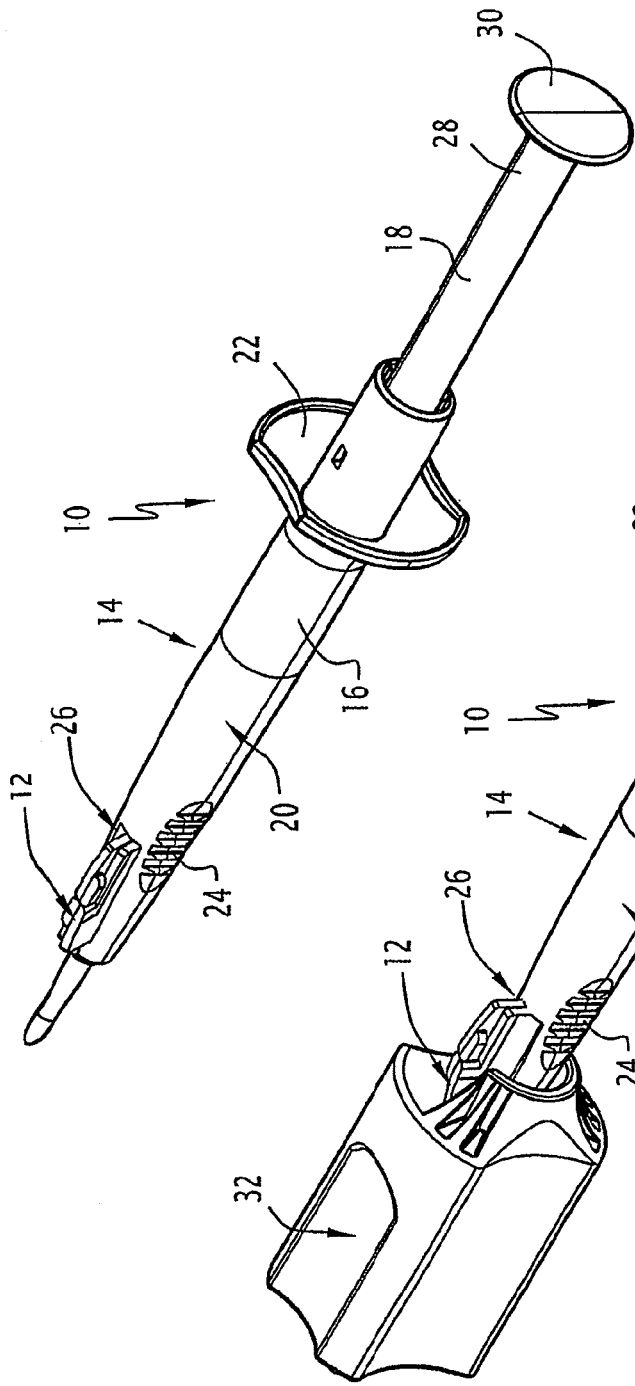
FIG. 1 is a perspective view of an ophthalmic implant injector provided with a cartridge ready for insertion.
Figure 4:
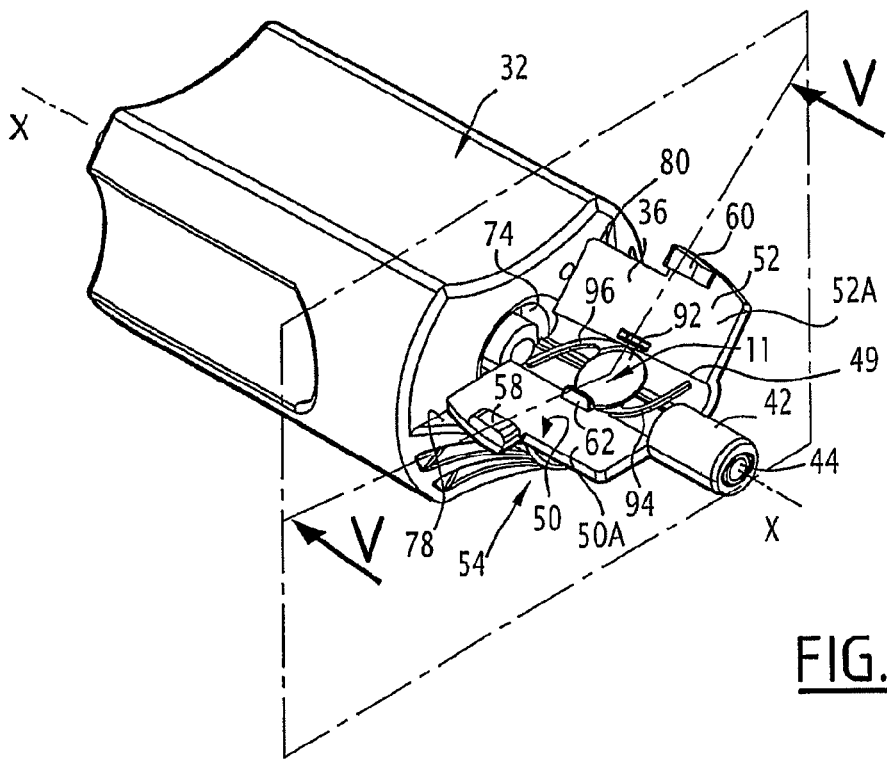
FIG. 4 is a perspective view of the folding cartridge received, in part, in the casing with the two arms being open and a implant being held between the two arms before being deformed.

The implant injector 10 shown in FIG. 1 is used to insert into the eye of a patient an ophthalmic implant 11 shown in FIG. 4 and comprises, in particular, a generally disc-shaped lens.

As is known per se, the injector comprises a folding cartridge 12 containing the implant to be inserted and an injection mechanism 14 formed from a tubular body 16 having, at one end, means for engaging the folding cartridge and a plunger 18 slidingly mounted through the body into the extension of the folding cartridge.

More precisely, the body 16 comprises a tube 20 having, at a rear end, a peripheral collar 22 forming a finger rest. At its other end, the tube 20 has non-slip impressions 24 which facilitate gripping of the tube. The tubular body 16 is split at its end opposite to the end through which the plunger 18 penetrates by a notch 26 for receiving a radial extension of the folding cartridge 12, allowing the cartridge 12 and the body 16 to be axially connected. Thus, at its end culminating at the end of the tube 20, the notch 26 has a narrow gap extended by a flared opening which allows the cartridge 12 and the body 16 to be connected in a bayonet-type manner.

The plunger 18 comprises an actuation rod 28 for passing right through the tube 20 and, at the rear end of the rod 28, a plate 30 forming a finger rest.

Figure 2:
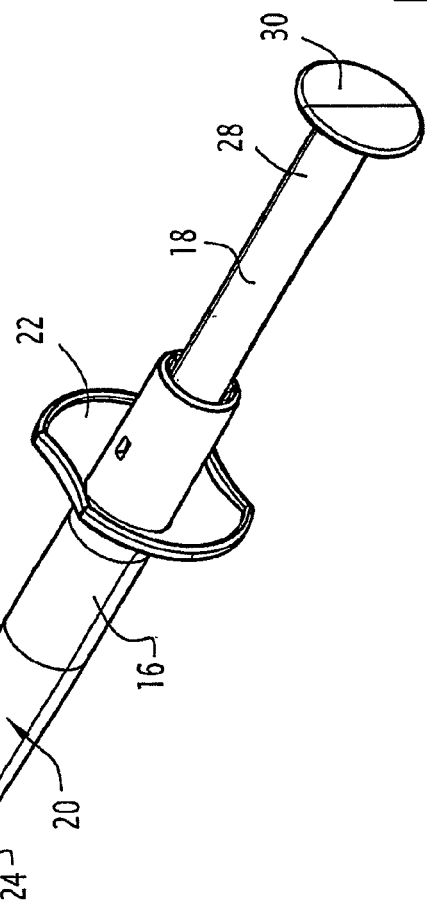
FIG. 2 is a perspective view of the injector shown in FIG. 1, the cartridge being covered, in part, by its protective casing.
Figure 3:
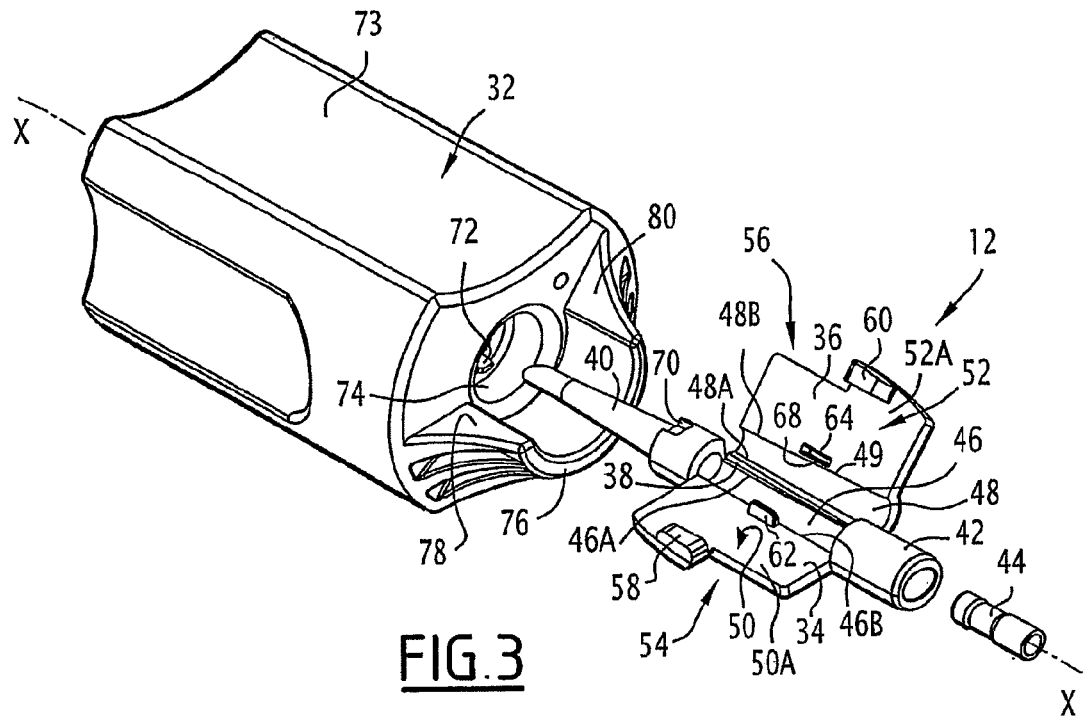
FIG. 3 is an exploded perspective view of the open folding cartridge, of the protective casing and of the piston.

As is shown in FIG. 2, the injector further comprises a casing 32 for protecting the insertion end of the folding cartridge. Said casing can be seen in FIG. 3 with the cartridge open.

The cartridge 12 comprises two arms 34, 36 articulated relative to one another about a hinge 38, of which the axis extends parallel to the axis X-X for inserting the implant defined by the cartridge. The two articulated arms are extended along the axis of insertion X-X, at one end, by a cannula 40 and, at the other end, by a sleeve 42 for receiving an insertion piston 44 to be displaced along the axis X-X when the plunger 18 is actuated.

More precisely, the two arms 34, 36 each have a channel 46, 48 next to the articulation 38. Said two channels extend parallel to one another and open opposite one another when the two arms are closed together. Said channels extend parallel to the direction of articulation of the hinge. They each have a semi-circular cross-section or, more precisely, a semi-elliptical cross-section.

The two arms are articulated in such a way that when the arms are moved away from one another the two channels 46, 48 extend substantially parallel to one another and transversely define two successive cavities. In contrast, when the two arms 34, 36 are closed together, the two channels 46, 48 are superimposed so as to form a conduit delimiting a closed contour.

The channels 46, 48 are longitudinally delimited by substantially parallel edges. Each channel is thus delimited by an inner wedge 46A, 48A arranged along the hinge 38. Said edges extend parallel to one another and are arranged in such a way that when the two arms 34, 36 are closed together, the two inner edges 46A, 48A are exactly aligned and meet, the two channels extending continuously and tangentially at the inner edges 46A, 48A which have been closed together.

The two channels 46, 48 are, on the other hand, delimited by two outer edges 46B, 48B provided at a distance from the articulation 38. The outer edges 46B, 48B are transversely displaced relative to the axis of the conduit, as will be described in detail hereinafter, in such a way that when the two arms are closed together, the two outer edges 46B, 48B are displaced towards one another without meeting, by forming between themselves a shoulder 49 shown in FIG. 6A.

In particular, the two edges 46B, 48B meet when the two arms are closed together at an end point arranged immediately at the exit of the sleeve 42. The edge 48B diverges from the edge 46B in the direction of the cannula 40 by the edge 48B diverting towards the inside of the conduit defined by the two channels.

The shoulder 49 is thus generally triangular or trapezoid, increasing in size towards the cannula 40.

Advantageously, the shoulder 49 is, on average, between 0.1 mm and 0.8 mm wide measured perpendicularly to the direction of the channels 46, 48. More precisely, and considering its triangular shape, it varies from 0 mm in size next to the sleeve 42 to between 0.2 and 1 mm in size and particularly equal to 0.4 mm in size at the cannula 40.

The shoulder 49 is flat. In order to provide the shoulder 49, the two channels are of different sizes, the edges 46A, 46B of the channel 46 being spaced further apart from the edges 48A, 48B of the channel 48 away from the sleeve 42.

Each arm 34, 36 has, beyond the channel 46, 48 associated from the side opposite the hinge 38, a maneuvering flange 50, 52. Said two flanges are generally rectangular. They have, opposite one another, planar bearing surfaces 50A, 52A to be applied one on the other when the two arms are closed together. Said flanges extend radially relative to the hinge 38. The shoulder 49 extends into the extension of the planar surface 52.

Following their free edge opposite the hinge 38, the flanges 50, 52 each comprise a notch 54, 56 arranged head to tail. In contrast, the flanges 50, 52 comprise, on the bearing surface 50A, 52A and to the right of the notch of the complementary flange, ratchet-type projections 58, 60. Said projections are to be received in the notches 54, 56 arranged on the opposing flange. Along their opposite end, they have complementary resilient interlocking profiles comprising associated projecting and hollow profiles allowing the two arms which have been closed together to be held one on the other, the channels constituting together a conduit with a closed cross-section.

Along the outer edges 46B, 48B of the channels, in the middle portion of the flanges 50, 52, a projection 62 is provided arranged on the flange 50 and a cavity of corresponding shape 64 is arranged in the flange 52 for receiving the projection 62.

The projection 62 extends the surface of the channel 46 to which it is tangentially connected.

In contrast, the cavity 64 is arranged at a distance from the edge 48B in such a way that a portion 66 of the shoulder 49 extends between the cavity 64 and the channel 48.

The piston 44 is fixed at the end of the plunger 18 and may run through the sleeve 42, the conduit delimited by the two channels 46, 48 and the cannula 40.

The sleeve 42 and the cannula 40 are arranged on either side of the channel 42. They extend said channel at each end and extend along the axis X-X of the channel.

The inner conduit of the sleeve 42 has a substantially circular cross-section and has a constant length.

The inner conduit delimited by the cannula 40 converges the channels 46, 48 towards the free end of the cannula. Inside, the cannula therefore has a conical surface with a tapering cross-section of the channels 46, 48 towards the insertion end.

Outside, the cannula 48 has two positioning notches 70 for cooperating with the projections 72 in the protective casing.

The protective casing 32 consists of a housing 73 with an opening 74 for inserting the cannula 40 arranged at the centre of an end face. The housing is longer than the cannula. Outside, the opening 74 is bordered on more than half of its periphery by a lip 76 having, at each end, bearing surfaces 78, 80 extending radially relative to the opening 74 and which may receive the flanges 50, 52 of the cartridge when the arms 34, 36 are moved away from one another as is shown in FIG. 4.

Figure 5:
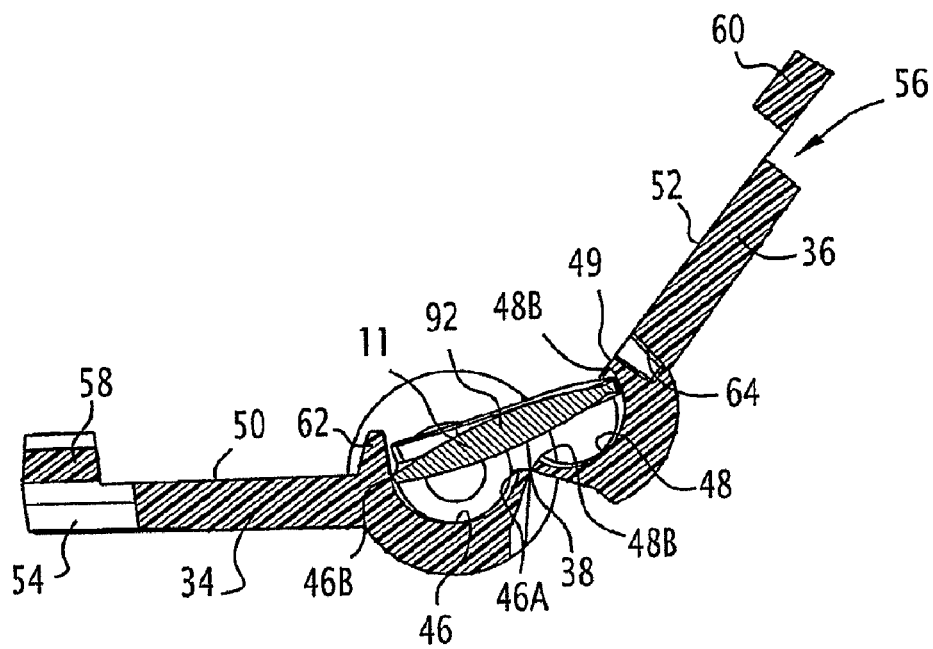
FIG. 5 is a transverse sectional view of the cartridge along the plane V-V shown in FIG. 4.

The folding cartridge 12 is shown in FIGS. 4 and 5 in an open position with an implant 11 arranged between the channels 46, 48. An implant of this type is, as is known per se, a lens 92 constituted by a transparent disc and two curved arms 94, 96 which are symmetrical about the axis of the lens. The two arms are diametrically opposed relative to the lens.

The implant is made of a resiliently deformable polymer material.

The implant is given its shape whilst the cannula of the cartridge is held in the protective casing, the two flanges resting on the surfaces 78, 80. The lens is placed so as to lie inside the channels 46, 48 in their middle portion, that is to say in the region of the projection 62 and the aperture 64, the two arms 94, 96 being arranged from the side of the sleeve 42 and from the side of cannula 40 respectively.

The implant is shown in this position in FIG. 4.

In this position, the implant 11 is in contact on either side with the surfaces of the channels 46, 48 and is supported by said channels at substantially diametrically opposed points.

It is to be understood that the closing together of the two arms 34, 36 by tilting about the articulation 38 provokes the folding of the implant 11 about an axis which is parallel to the axis of the channels 46, 48 when said folding is initiated by the surgeon pressing, for example by means of a clamp, at the centre of the implant. In particular, the central portion of the lens is applied on the hinge 38 when the opposite edges of the lens are brought together in contact with the channels 46, 48 as shown in FIG. 6 when the two arms are closed together.

Figure 7:
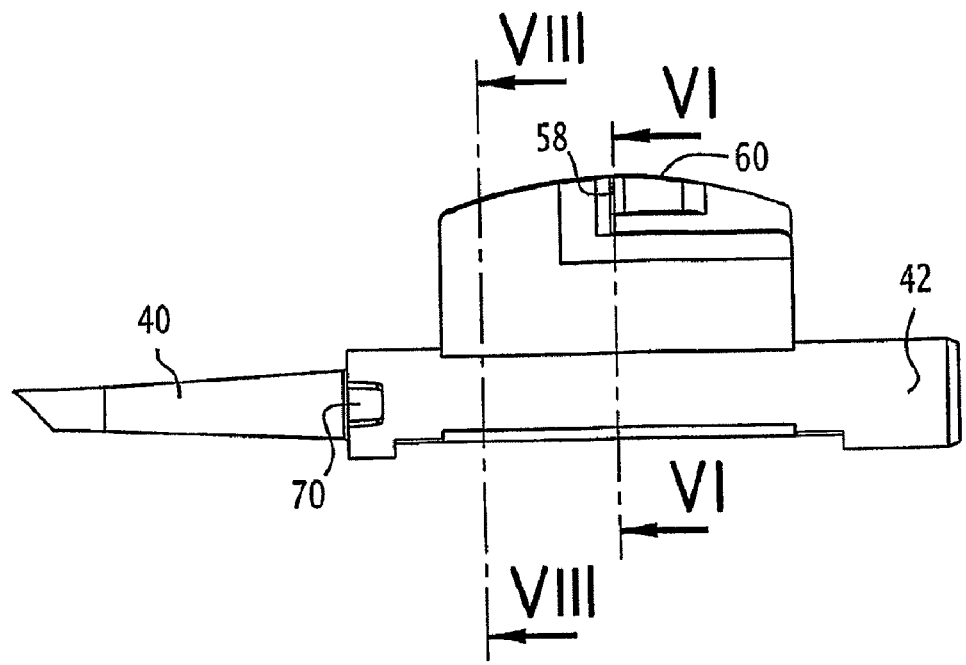
FIG. 7 is an elevated view of the folding cartridge once it has been closed again.

In this position and as illustrated in FIG. 7, the two arms are held together by cooperation of the engagement profiles 58, 60.

Figures 6, 6A:
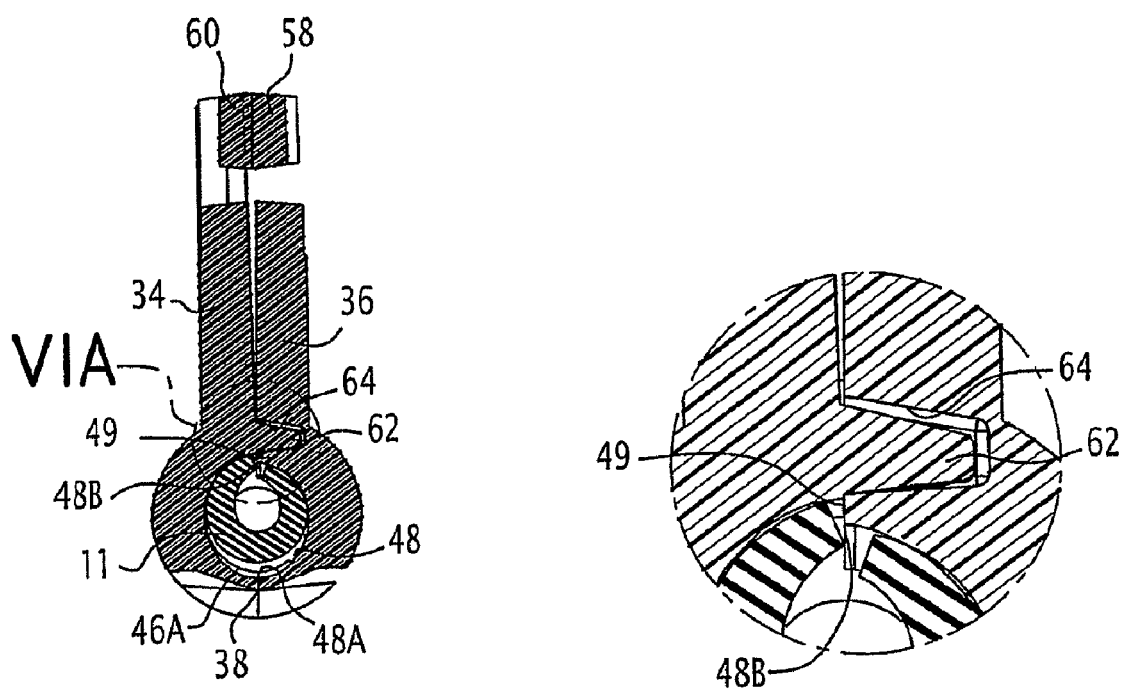
FIG. 6 is a sectional view of the cartridge along line VI-VI shown in FIG. 7.
FIG. 6A is an enlarged view of a part shown in FIG. 6.

In the position shown in FIG. 6, the edge of the lens from the side of the channels 46 rests against the surface of the flange 52 forming the shoulder 49 and projecting inside the conduit delimited by the two channels 46, 48. In contrast, the end of the lens resting against the channel 48 is lightly bent inside the opposite end of the lens, thus producing the curling of the spiral of the lens.

Figure 8:
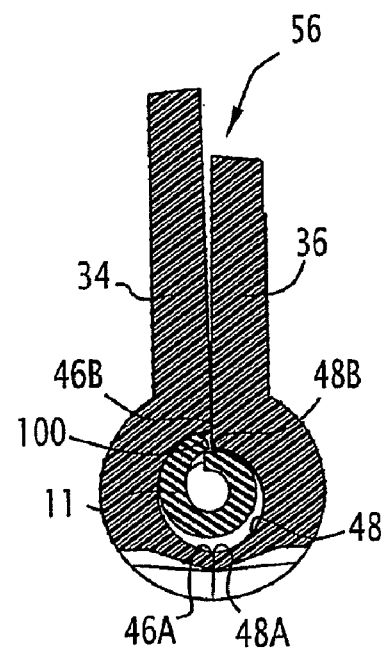
FIG. 8 is a sectional view of the cartridge along line VIII-VIII shown in FIG. 6 during displacement of the implant.

As shown in FIG. 8, the shoulder 49 extends substantially along the length of the channels 46, 48. Thus, when the lens 92 is displaced under action of the piston 44 through the conduit, the opposite edges of the lens overlap ensuring that the edge resting against the shoulder 49 is outside the edge bent back by the channel 48 by means of the shoulder 49.

The presence of the shoulder 49 ensures that, when the implant is compressed through the channel and when the implant is curled in a spiral, the opposite ends are correctly radially displaced and superimposed allowing the implant to curl satisfactorily on itself without the two edges pressing against one another. Furthermore, the direction of curling of the implant is ensured since it is forced by the shape of the channels 46, 48 and the presence of the shoulder 49.

Figure 9:
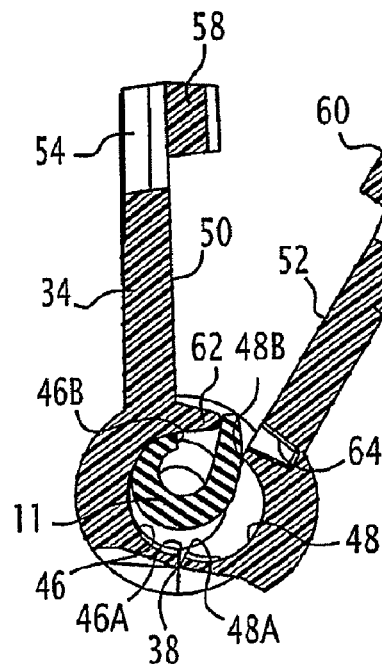
FIG. 9 is a transverse sectional view of the folding cartridge when the two arms are closed together showing bad positioning of the implant.

It is also to be understood that the presence of the projection 62 and the complementary aperture 64 ensures that, if the implant is initially badly positioned, it is difficult to bring the two flanges together, as shown in FIG. 9. In fact, if one of the edges of the implant escapes from one of the channels 46, 48 said edge constitutes a barrier between the projection 62 and the cavity 64, stopping the projection from penetrating into the aperture. The surgeon thus feels a hard point when trying to bring the two arms together and is thus aware that the implant is badly positioned.

In contrast, if the implant is positioned correctly, as shown in FIG. 7, the projection 62 is received completely in the cavity 64.

The invention claimed is:

1. A cartridge (12) for folding an ophthalmic implant (11) comprising:
a clamp formed by two articulated arms (34, 36), said two arms (34, 36) having substantially coaxial channels (46, 48), each of which is bordered by two longitudinal edges (46A, 46B, 48A, 48B), the channels (46, 48) opening opposite one another and, when the two arms (34, 36) are closed together, defining a conduit for containing the partially folded implant (11),
characterised in that when said two arms (34, 36) are closed together, at least two of the edges (46B, 48B) facing the two channels (46, 48) are transversely displaced relative to the conduit in the joining plane of said two arms (34, 36) in such a way that one arm (36) defines a flat shoulder (49) between said two edges (46B, 48B), the shoulder (49) extending from one edge (46B) to the other edge (48B), the shoulder (49) supporting the implant (11) in a manner that ensures that opposite ends of the implant (11) are correctly radially displaced and superimposed, the shoulder (49) projecting opposite the channel (46) arranged in the other arm (34), and in that one (48B) of the two edges (46B, 48B) defining the shoulder (49) diverges from the other edge (46B) in the direction of an end of the cartridge (12), said one edge (48B) diverting towards the inside of the conduit defined by the two channels (46, 48).

2. The cartridge according to claim 1, characterised in that the shoulder (49) is on average between 0.1 and 0.8 mm wide in the joining plane, measured transversely to the direction of the channels.

3. The cartridge according to claim 1, characterised in that the two displaced edges (46B, 48B) are further away from an axis of articulation (38) of the two arms (34, 36) than the two other edges (46A, 48A) which meet when the two arms (34, 36) are closed together.

4. The cartridge according to claim 1, characterised in that the cartridge comprises an injection cannula (40), of which the internal surface converges inside the extension of the conduit containing the implant (11) when the two arms are closed together.

5. The cartridge according to claim 1, characterised in that the two channels (46, 48) have a substantially semi-circular or semi-elliptical cross-section.

6. The cartridge according to claim 1, characterised in that the shoulder (49) is substantially planar and the axis of the conduit formed by the two channels (46, 48) extends substantially into the plane defined by the shoulder (49).

7. The cartridge according to claim 3, characterised in that each arm (34, 36) has, beyond the channel (34, 36) and on the side opposite the axis of articulation (38), a maneuvering flange (50, 52), and the shoulder (49) extends in the plane of a flange (52) for maneuvering one of the arms (48).

8. The cartridge according to claim 1, characterised in that the two arms (34, 36) comprise, next to the edges (48A, 48B) of the channels and outside the channels, complementary projecting and hollow connection profiles (62, 64), distinct from the shoulder (49), which are of such a size that the profiles fit together when the two arms (34, 36) are closed together.

9. An implant injector comprising a cartridge according to claim 1, and an injection mechanism comprising a body for linking to the cartridge and a plunger capable of pushing the implant contained inside the cartridge.

10. The cartridge according to claim 4, characterized in that the shoulder (49) has a general triangular shape with a width that increases in size towards the cannula (40).

* * * * *